United States Patent

Wu et al.

[11] Patent Number: 5,707,921
[45] Date of Patent: *Jan. 13, 1998

[54] METHOD OF PREPARING ISOMERIZATION CATALYST COMPOSITION

[75] Inventors: An-hsiang Wu, Bartlesville; Charles A. Drake, Nowata; Ralph J. Melton, Bartlesville, all of Okla.

[73] Assignee: Phillips Petroleum Company, Bartlesville, Okla.

[*] Notice: The term of this patent shall not extend beyond the expiration date of Pat. No. 5,591,689.

[21] Appl. No.: 529,179

[22] Filed: Sep. 15, 1995

[51] Int. Cl.$^6$ .................................. B01J 23/42
[52] U.S. Cl. ..................... 502/334; 502/326; 502/327; 502/333; 502/335
[58] Field of Search ........................... 502/229, 230, 502/231, 326, 327, 333, 334, 335

[56] References Cited

U.S. PATENT DOCUMENTS

| | | | |
|---|---|---|---|
| 3,112,351 | 11/1963 | Hoekstra et al. | 260/683.75 |
| 3,242,228 | 3/1966 | Riordan et al. | 260/683.68 |
| 3,963,643 | 6/1976 | Germanas et al. | 252/442 |
| 4,014,948 | 3/1977 | Myers | 208/112 |
| 4,149,993 | 4/1979 | Rao et al. | 252/442 |
| 5,004,859 | 4/1991 | Schmidt et al. | 585/741 |
| 5,591,689 | 1/1997 | Wu et al. | 502/334 |

*Primary Examiner*—Glenn Caldarola
*Assistant Examiner*—Alexander G. Ghyka
*Attorney, Agent, or Firm*—Charles W. Stewart

[57] ABSTRACT

A Group VIII metal- and chloride-containing composition (effective as an alkane/cycloalkane isomerization catalyst) is prepared by a method which comprises mixing at least one aluminum- and chlorine-containing compound (preferably AlCl$_3$) with a solid material containing at least one Group VIII metal (Pt and/or Pd and/or Ni) and alumina, heating the obtained solid mixture in an inert gas, and then treating the solid mixture with a gas mixture comprising hydrogen gas and HCl and/or chloroalkane (such as CCl$_4$).

19 Claims, No Drawings

METHOD OF PREPARING ISOMERIZATION CATALYST COMPOSITION

BACKGROUND OF THE INVENTION

This invention relates to the preparation of Group VIII metal-containing catalyst compositions, which are effective as catalysts for isomerizing saturated $C_4$–$C_8$ hydrocarbons.

Supported Group VIII metal- and chloride-containing compositions for alkane isomerization reactions are well known, and are described in the patent literature, e.g., in U.S. Pat. Nos. 5,004,859 and 4,149,993. However, there are ever present incentives for the development of new, effective methods of preparing them.

SUMMARY OF THE INVENTION

It is an object of this invention to provide a novel method for preparing supported, Group VIII metal- and chloride-containing catalyst compositions. It is a specific object of this invention to prepare a catalyst composition which comprises platinum, chloride and alumina. It is another specific object of this invention to prepare a catalyst composition which comprises palladium, chloride and alumina. It is still another specific objective to prepare a catalyst composition comprising nickel, chloride and alumina. Other objects and advantages will become apparent from the detailed description and the appended claims.

In accordance with this invention, a method of preparing a solid Group VIII metal- and chlorine-containing composition comprises:

(1) mixing at least one aluminum- and chlorine-containing compound selected from the group consisting of aluminum chloride ($AlCl_3$) and alkylaluminum chlorides with a solid material which comprises (i) at least one Group VIII metal selected from the group consisting of platinum, palladium and nickel and (ii) alumina as the support;

(2) heating the mixture obtained in step (1) in a substantially inert gas atmosphere at a temperature of about 450°–700° C. for a time period of at least about 10 minutes; and (3) treating the material obtained in step (2) with a gas mixture comprising hydrogen gas and at least one chlorine-containing compound selected from the group consisting of hydrogen chloride and chloroalkanes, at a temperature of about 50°–700° C. for a time period of at least about 10 minutes.

Preferably, the solid material comprising components (i) and (ii) which is used in step (1) has been prepared by a method comprising:

(a) impregnating an alumina material with at least one compound of a Group VIII metal selected from the group consisting of platinum, palladium and nickel;

(b) calcining the impregnated alumina obtained in step (a) at a temperature of about 300°–650° C. for a time period of at least about 10 minutes; and (c) treating the calcined material obtained in step (b) with a reducing gas (preferably a free-hydrogen-containing gas) at a temperature of about 200°–550° C. for a time period of at least about 10 minutes.

DETAILED DESCRIPTION OF THE INVENTION

Any suitable alumina material can be used in step (a) of the preparation method of this invention. Suitable aluminas include (but are not limited to) hydrated aluminas (such as beohmite, pseudoboehmite, bayerite), alpha-alumina, beta-alumina, gamma-alumina, delta-alumina, eta-alumina and theta-alumina, preferably gamma-alumina. The alumina material generally has a surface area (determined by the BET method of Brunauer, Emmett and Teller employing $N_2$) of about 100–400 $m^2/g$, a pore volume (measured by nitrogen intrusion porosimetry) of about 0.2–1.0 $cm^3/g$, and a particle size of about 8–200 mesh. The alumina particles can be spherical, cylindrical, trilobal, or can have any other suitable shape. The presently preferred alumina particles are cylindrical extrudates. A preferred alumina material consists essentially of $Al_2O_3$. However, it is within the scope of this invention to have small mounts of at least one titanium compound (generally as $TiO_2$, at a level of about 0.05–1 weight-% Ti) present in the alumina material used in step (a).

Any suitable platinum compound (preferably water-soluble) can be used as the at least one Group VIII metal compound in step (a) of the preparation method of this invention. Suitable Pt compounds include (but are not limited to) platinum(II) chloride, platinum(IV) chloride, hexachloroplatinic(IV) acid, ammonium hexachloroplatinate(IV), tetrammineplatinum(II) chloride, tetrammineplatinum(II) carbonate, tetrammineplatinum(II) hydroxide, dichlorodiammineplatinum(II), tetrachlorodiammineplatinum(IV), platinum(II) nitrate, platinum(IV) nitrate, hexammineplatinum(II) nitrate, hexammineplatinum(IV) nitrate, diammineplatinum(IV) nitrite, diammineplatinum(II) oxalate, and many other complex (coordination) compounds of divalent and tetravalent platinum. Presently preferred is hexachloroplatinic acid, $H_2PtCl_6$.

Any suitable palladium compound (preferably water-soluble) can be used as the at least one Group VIII metal compound in step (a) of the preparation method of this invention. Suitable Pd compounds include (but are not limited to) palladium (II) chloride, palladium(II) nitrate, palladium(II) sulfate, palladium(IV) chloride, hexachloropalladic(IV) acid ($H_2PdCl_6$), ammonium hexachloropalladate(IV), tetramminepalladium(II) nitrate, tetramminepalladium(II) chloride, tetramminepalladium (IV) nitrate, tetrammine palladium(IV) chloride, and other coordination compounds of divalent and tetravalent palladium.

Any suitable nickel compound (preferably water-soluble) can be used as the at least one Group VIII metal compound in step (a) of the preparation method of this invention. Suitable Ni compounds include (but are not limited to) nickel(II) chloride, nickel(II) nitrate, nickel(II) sulfate, ammonium nickel(II) sulfate, nickel(II) acetate, nickel(II) oxalate, hexamminenickel(II) chloride, hexamminenickel (II) nitrate, hexamminenickel(II) sulfate, and other coordination compounds of divalent nickel. Presently preferred is nickel(II) nitrate, more preferably $Ni(NO_3)_2 \cdot 6H_2O$.

It is within the scope of this invention to have a dissolved titanium compound also present in step (a) of the preparation method of this invention, in particular when the alumina contains no Ti. Any soluble (preferably water soluble) titanium compound can be used in step (a), either before or simultaneously with or after the impregnation with at least one compound of at least one Group VIII metal (more preferably platinum). Suitable Ti compounds which can be employed in this embodiment include (but are not limited to) titanium halides (such as $TiCl_4$), tetraalkyl titanates of the general formula $Ti(OR)_4$ wherein each R is an alkyl group (such as tetraethyl titanate, tetra-n-propyl titanate, tetraisopropyl titanate, tetrabutyl titanates), and water-soluble alkanolamine titanates (such as those described in U.S. Pat. Nos. 2,824,114; 2,935,522; 2,950,174; 3,028,297; 3,694,475; 3,892,791 and 4,621,148). These latter compounds are generally prepared by the reaction of 1 mole of a tetraalkyl titanate with 1–4 (preferably 2) moles of an alkanolamine selected from the group consisting of ethanolamine, diethanolamine, triethanolamine (preferred), monoisopropylamine, diisopropylamine and triisopropylamine. Each of the alkyl (R) groups (which may be the same as or different from one another) of the tetraalkyl titanate, $Ti(OR)_4$, generally contains 2–4 carbon atoms, and preferably is the isopropyl group. A particular alkanolamine titanate which can be used in step (a) of the method of this invention is prepared by the reaction of 1 mole of tetraisopropyl titanate, $Ti(OC_3H_7)_4$, with 2 moles of triethanolamine, also referred to as tri(2-hydroxyethyl) amine, thus forming primarily diisopropyl-bis (triethanolamine) titanate. A solution containing 80 weight-% of diisopropyl-bis(triethanolamine) titanate and 20 weight-% of isopropanol is commercially available from DuPont de Nemours and Co., Wilmington, Del., under the product designation of "TYZOR" TE TITANATE (wherein "TYZOR" is a registered trademark of DuPont).

The alumina material can be impregnated in step (a) with at least one dissolved Group VIII metal compound in any suitable manner, such as by incipient wetness impregnation, or by spraying with an impregnating solution containing at least one dissolved Group VIII metal compound. Generally, the total concentration of the at least one Group VIII metal compound (i.e., at least one Pt compound or at least one Pd compound or at least one Ni compound or mixtures of compounds of different Group VIII metals) in the impregnating solution generally is in the range of about 0.01–2 mol/l. Preferably, the solvent of the impregnating solution is an alcohol (such as ethanol) and/or water (the latter being presently preferred). For some Group VIII metal compounds (such as $H_2PtCl_6$) it is preferred to employ as solvent slightly acidified water (e.g., a solution of HCl in $H_2O$ having a pH of about 1–3). If it is desired to also impregnate the alumina with at least one Ti compound (in particular, when the at least one Group VIII metal compound is at least one Pt compound), this can be done before or concurrently with or after the impregnation with the at least one Group VIII metal compound. The concentration of the Ti compound in the impregnating solution generally is about 0.01–2 mol/l. The solvent of this impregnating solution can be water and/or an alcohol (such as ethanol) or any other suitable liquid in which the particular Ti compound is soluble and stable. The weight ratio of the Group VIII metal-containing impregnating solution to alumina in step (a) is such as to attain a weight percentage of about 0.1–10 (preferably about 0.2–5) weight-% Group VIII metal (on an elemental basis) in the finished composition (i.e., the material obtained in the last step of the preparation method of this invention). If impregnation with at least one Ti compound is also carried out, the weight ratio of the Ti-containing impregnating solution to the alumina material generally is such as to attain a weight percentage of about 0.05–1.0 weight-% Ti (on an elemental basis) in the finished composition.

In step (b), the Group VIII metal impregnated alumina material is heated (calcined) at a temperature of about 300°–650° C. (preferably 450°–550° C.), generally for a time period of about 0.5–20 hours (preferably about 2–4 hours). This calcining step can be done in an inert atmosphere (e.g., $N_2$, He, Ne, Ar and the like) or in an $O_2$-containing atmosphere (e.g., air). Preferably, a drying step (generally at about 80°–150° C.) precedes heating step (b).

In step (c), the calcined material obtained in step (b) is treated with a reducing gas, generally a gas (preferably a gas stream) which generally comprises (preferably consists essentially of) free hydrogen ($H_2$), generally at a temperature of about 200°–550° C. (preferably about 350°–450° C.) for a time period of about 0.5–10 hours. Other, less preferred reducing gases include (but are not limited to) carbon monoxide, $C_1$–$C_6$ alkanes, and $C_2$–$C_6$ alkenes and $C_4$–$C_6$ alkadienes.

In step (1) of the preparation method of this invention, at least one dry aluminum- and chlorine-containing compound is mixed with a Group VIII metal-containing alumina material, preferably one having been obtained by the above-described method comprising steps (a)–(c). Generally, the weight ratio of the Al- and Cl-containing compound (preferably $AlCl_3$) to the Group VIII metal-impregnated alumina material is in the range of about 0.05:1 to about 1:1, preferably about 0.1:1 to about 0.3:1. When the preferred Al- and Cl-containing compound, $AlCl_3$, is used in step (1), it is generally applied as a dry powder which is mixed with the Group VIII metal-impregnated alumina, preferably in a dry, inert gas environment.

Other, less preferred Al- and Cl-containing compounds which can be used in step (1) include (but are not limited to) alkylaluminum chlorides such as methylaluminum dichloride, methylaluminum sesquichloride, dimethylaluminum chloride, ethylaluminum dichloride, ethylaluminum sesquichloride, dimethylaluminum chloride, propylaluminum dichloride, dipropylaluminum chloride, butylaluminum dichloride, dibutylaluminum chloride, and mixtures thereof. Mixtures of $AlCl_3$ and any of the above alkylaluminum chlorides can also be used. Since the above-listed alkylaluminum chlorides are easily hydrolyzed, they should be handled and applied to alumina in a dry, inert gas environment. Generally, at least one alkylaluminum chloride is dissolved in an essentially water-free solvent, and the Group VIII metal-containing alumina is then impregnated with the obtained solution (which generally contains about 5–50 weight-% of the alkylaluminum chloride) at a temperature of about 10°–50° C. for a time period of about 0.5–5 hours (preferably about 1–2 hours). The solvent in which the alkyl-Al chloride is dissolved generally is a dry organic hydrocarbon solvent, such as cyclohexane, benzene, toluene, xylenes or mixtures thereof. It is within the scope of this invention (yet less preferred) to vaporize the alkylaluminum chloride and contact the thus-vaporized compound with the Group VIII-metal coming alumina at the above-recited weight ratio. It is also within the scope of this invention to have at least one titanium compound present in step (1). Suitable titanium compounds include (but are not limited to) those listed for step (a). The amount of the Ti compound(s) which can be used in step (1) is such as to obtain a material in step (3) which contains about 0.05–1.0 weight-% Ti.

In step (2), the mixture obtained in the previous step is heated to a temperature at about 450°–700° C. (preferably about 625°–675° C.), generally for a period of time of about 0.5–20 hours (preferably about 0.5–2 hours). This heating is carried out in an inert gas stream (e.g., $N_2$, He, Ar), preferably in an upflow mode. It is presently preferred to carry out preliminary heating steps (more preferably in upflow inert gas streams) before step (2): heating the mixture obtained in step (1) from room temperature (about 10°–40° C.) to a temperature of about 200°–250° C. within a time period of about 0.5–5 hours, heating the material at about 200°–250° C. for a time period of about 1–20 hours, and increasing the temperature from about 200°–250° C. to about 450°–700° C.

(more preferably about 625°–675° C.) within a time period of about 0.5–3 hours. A particularly preferred mode of operation is described in Example IV.

Chlorination step (3) is carried out by heating with a gas comprising $H_2$ and at least one chlorine-containing compound which can be HCl or at least one chloroalkane or a mixture of any of these chloriding agents. Suitable chloroalkane generally contain 1–4 carbon atoms per molecule and 1–6 chlorine atoms per molecule. Examples of suitable chloroalkanes include (but are not limited to) chloromethane, dichloromethane, trichloromethane (chloroform), carbon tetrachloride, chloroethane, 1,1-dichloroethane, 1,2-dichloroethane, trichloroethanes, tetrachloroethanes, hexachloroethane, 1-chloropropane, 2-chloropropane, 1,2-dichloropropane, 1,3-dichloropropane, 2,2-dichloropropane, trichloropropanes, tetrachloropropanes, chlorobutanes, 1-chloro-2-methylpropane, dichlorobutanes, trichlorobutanes, tetrachlorobutanes, and the like, and mixtures thereof. Carbon tetrachloride is the presently preferred chloroalkane.

The molar ratio of $H_2$ to the at least one chlorine-containing compound used in step (3) generally is about 0.01:1 to about 100:1, preferably about 0.05:1 to about 50:1, more preferably about 0.2:1 to about 20:1. It is within the scope of this invention to have an inert diluent (such as $N_2$, He, Ne, Ar) present in the chloriding gas mixture of step (3). Treatment step (3) is carried out at a temperature of about 50°–700° C. (preferably about 150°–400° C., more preferably about 180°–280° C., most preferably about 200°–250° C.) for a period of time of about 0.2–20 hours (preferably about 0.5–2 hours). The thus-chlorided material generally is cooled to room temperature (about 10°–40° C.), preferably in an inert gas atmosphere. Preferably, step (3) is carried out in an upflow mode, which generally results in a more uniform finished catalyst. It is within the scope of this invention to carry out step (3) in an alkane isomerization reactor (which may be located in an oil refinery or a petrochemical plant), whereas the preceding preparation steps generally are carried out in equipment located on premises of a catalyst manufacturer.

The finished catalyst composition obtained in step (3) generally comprises about 0.1–8 (preferably about 0.2–3) weight-% of Group VIII metal (Pt and/or Pd and/or Ni) and about 2–7 (preferably about 3–6) weight-% Cl (chemically bound as chloride). The surface area, pore volume, shape and particle size of the finished catalyst composition are approximately the same as those of the alumina starting material (recited above).

The catalyst prepared by the method of this invention can be employed in the isomerization of saturated $C_4$–$C_8$ hydrocarbons (alkanes and/or cycloalkanes, preferably normal alkanes). Examples of suitable feed hydrocarbons include (but are not limited to) normal butane, normal pentane, normal hexane, normal heptane, normal octane, cyclohexane, methylcyclopentane, cycloheptane and methylcycloheptane (more preferably n-butane), generally in the presence of hydrogen. These so-called hydroisomerization processes are well known and have been described in the patent literature (e.g., in U.S. Pat. Nos. 4,149,993 and 5,004,859). Generally, hydrogen is mixed with the saturated feed hydrocarbon to form a feed mixture which is contacted with the isomerization catalyst of this invention contained in an isomerization zone. The concentration of the hydrogen in the feed mixture during this contacting step shall be such as to provide a hydrogen:hydrocarbon molar ratio of at least about 0.01:1, generally about 0.01:1 to about 5:1, preferably about 0.02:1 to about 2:1. The basic isomerization reaction conditions are well known and can be varied to achieve the desired conversion of the feed hydrocarbon to the desired isomer in a manner known in the art. Also, the recovery of the product isomer from the reaction mixture can be carried out by any suitable separation technique, such as fractional distillation. Isomerization of normal butane (n-butane) to isobutane is the presently preferred reaction carried out with the catalyst composition of this invention.

Generally, the saturated feed hydrocarbon and $H_2$ are contacted with the catalyst (generally present in a fixed bed) at a reaction temperature of at least about 200° F., preferably at a temperature of about 200°–500° F. In the preferred case of n-butane isomerization, the temperature is generally about 250°–400° F. Generally, the liquid hourly space velocity of the saturated hydrocarbon feed stream, i.e., cc of liquid feed hydrocarbon per cc of catalyst per hour, is about 0.1 to about 15. Generally, the reaction pressure is within the range of 200 psig to about 1500 psig in the isomerization zone. The gas hourly space velocity of the hydrogen feed stream is generally about 10–2,000 (preferably about 50–950) cc $H_2$ per cc catalyst per hour (so as to give the above-recited $H_2$:hydrocarbon ratio). In order to activate the catalyst and to retard its deactivation during the isomerization reaction, about 0.001 to about 1 weight percent chloride is frequently added to the alkane feed, generally in the form of at least one chloroalkane (described above), preferably carbon tetrachloride, chloroform, ethyl chloride or isopropyl chloride.

When the catalyst, after it has been in use in the hydroisomerization process, has lost its activity to the extent that the desired alkane conversion can no longer be attained at the desired reaction temperature, the catalyst can be reactivated by turning off the flow of the saturated feed hydrocarbon while maintaining the flow of the $H_2$ stream through the isomerization catalyst, generally at about the same gas hourly space velocity of $H_2$ as in the isomerization reaction. The temperature in this reactivation step is generally about the same as in the isomerization reaction, but may be readjusted upward or downward to maximize the reactivation effect. In this reactivation step, a reducing gas stream consisting essentially of hydrogen can be passed through the partially deactivated isomerization catalyst bed at a temperature of about 80°–350° F. (preferably about 250°–330° F.) and a GHSV (gas hourly space velocity) of about 10–2,000 cc $H_2$ per cc catalyst per hour (more preferably about 50–950 cc/cc/hour), for a time period of about 2 hours to about 10 days (more preferably about 5 hours to about 7 days). Thereafter, the reactivated catalyst can be redeployed in the alkane hydroisomerization of saturated $C_4$–$C_8$ hydrocarbons, as described above.

The following examples are provided to further illustrate this invention and are not to be considered as unduly limiting the scope of this invention.

EXAMPLE I

This example illustrates the preparation of several chlorinated platinum/alumina compositions (useful as catalysts for the isomerization of alkanes and/or cycloalkanes).

Catalyst A (Invention) contained 0.320 weight-% Pt and was prepared as follows. A Pt-promoted alumina, provided by United Catalysts, Inc. (UCI; Louisville, Ky.) under the product designation "UCI-331" was first calcined for 6 hours in air at 525° C. Thereafter, the temperature was lowered to 400° C., and the calcined material was heated for 2 hours at 400° C. in a pure hydrogen gas stream. About 12 grams of the thus-reduced Pt/$Al_2O_3$ material is then mixed with 2.0 grams of dry aluminum chloride (AlCl$_3$). The obtained solid mixture was heated in a helium stream (flow rate: 40 cc/minute) so as to raise its temperature from room temperature to 650° C. at a rate of about 10° C./minute, heated for 2 hours at 650° C. in the above He gas stream, cooled in the above He gas stream to 225° C., heated for 1 hour in a hydrogen/HCl gas mixture (flow rate of H$_2$:30 cc/minute; flow rate of HCl: 30 cc/minute), and cooled in the above H$_2$/HCl gas mixture to 100° C.

Catalyst B (Control) contained 0.320 weight-% Pt and was prepared substantially in accordance with the procedure for Catalyst A, except that a helium/HCl gas mixture (flow rate of He:30 cc/minute; flow rate of HCl:30 cc/minute) used (in lieu of the H$_2$/HCl mixture) for the chloriding step at 225° C. and for the final cooling step (225° C.→100° C.).

Catalyst C (Invention) contained 0.320 weight-% Pt and was prepared substantially in accordance with the procedure for Catalyst A, except that a hydrogen/CCl$_4$ gas mixture (flow rate of H$_2$:30 cc/minute; bubbled through liquid CCl$_4$; thus essentially saturated with CCl$_4$ vapor) was used (in lieu of H$_2$/HCl) for the chloriding step at 225° C. and for the final cooling step (225° C.→150° C.).

Catalyst D (Control) contained 0.320 weight-% Pt and was prepared substantially in accordance with the procedure for Catalyst A, except that a helium/CCl$_4$ gas mixture (flow rate of He: 30 cc/minute; bubbled through liquid CCl$_4$; thus essentially saturated with CCl$_4$ vapor) was used (in lieu of H$_2$/HCl) for the chloriding step at 225° C. and for the final cooling step (225° C.→150° C.).

Catalyst E (Invention) contained 0.304 weight-% Pt and was prepared substantially in accordance with the procedure for Catalyst C, except that the Pt/Al$_2$O$_3$ starting material was prepared in the laboratory by impregnating 45.0 grams of gamma-alumina (provided by Criterion Catalyst Company, Houston, Tex.) by incipient wetness at room temperature in an air atmosphere with an aqueous platinum-containing solution containing 0.36 g H$_2$PtCl$_6$, 0.36 g HCl and 25.0 g H$_2$O, followed by air-drying the Pt-impregnated material (first under vacuum conditions at room temperature, then in air at about 125° C.), calcining it for 6 hours in air at about 252° C., and reducing it for 2 hours in flowing hydrogen gas at 400° C. 14.6 grams of the thus-reduced Pt/Al$_2$O$_3$ material was then mixed with 2.0 dry AlCl$_3$, and the solid mixture was heated in He (at 650° C.) and thereafter in H$_2$/HCl (at 225° C.), essentially as described for Catalyst C.

EXAMPLE II

This example illustrates the performance of the catalyst compositions described in Example I in the isomerization of n-butane.

20 cc of each catalyst was placed in a stainless steel reactor tube having an inner diameter of 1 inch and a length of 28 inches. The steel reactor tube was heated to about 138° C. A stream of hydrogen gas was passed through the catalyst bed at a rate of 1.34 cubic feet per hour. The reactor pressure was adjusted to about 500 psig. Liquid n-butane was introduced at a rate of about 80 cc/hour (liquid hourly space velocity: about 4.0 cc/cc catalyst/hour), while the flow of the hydrogen gas stream was maintained at about 1.31 ft$^3$/hour so as to provide a molar ratio of H$_2$ to n-butane of about 50:1. After the hydrogen/n-butane mixture had passed through the catalyst bed at the above conditions for about 10 minutes, carbon tetrachloride was injected into this feed mixture at a rate of 16 microliters per hour for a time period of up to 22–24 hours. Thereafter, the CCl$_4$ feed rate was reduced to 6 microliters per hour, and the test was continued. The isomerization product was analyzed by means of a gas chromatograph. Pertinent catalyst preparation parameters and isomerization test results (obtained at comparable reaction times) are summarized in Table I.

TABLE I

| Catalyst | Wt % Promoter(s) in Catalyst | First Chlorination | | Second Chlorination | | n-Butane Isomerization | |
|---|---|---|---|---|---|---|---|
| | | Agent | Temp. (°C.) | Agent | Temp. (°C.) | Reaction Time (hr.) | % of Isobutane in Product |
| A (Invention) | 0.320 % Pt | AlCl$_3$ | 650 | H$_2$/HCl | 225 | 24 | 12.2 |
| B (Control) | 0.320 % Pt | AlCl$_3$ | 650 | He/HCl | 225 | 24 | 8.2 |
| C (Invention) | 0.320 % pt | AlCl$_3$ | 650 | H$_2$/CCl$_4$ | 225 | 24 | 12.3 |
| D (Control) | 0.320 % Pt | AlCl$_3$ | 650 | He/CCl$_4$ | 225 | 24 | 7.6 |
| E (Invention) | 0.304 % Pt | AlCl$_3$ | 650 | H$_2$/CCl$_4$ | 225 | 24 | 14.7 |

Test data in Table I clearly show that the catalysts prepared by the method of this invention (comprising chlorination with aluminum chloride and subsequent chlorination with either H$_2$/HCl or H$_2$/CCl$_4$) were significantly more active as n-butane isomerization catalysts than those prepared by a method comprising chlorination with either He/HCl or He/CCl$_4$. Additional tests (carried out in autoclaves at room temperature, not described herein in detail) indicated that Invention Catalysts A, C and E were also more effective as catalysts for the isomerization of n-hexane to isohexanes. Further autoclave tests indicated that all tested catalysts (A thru E) were approximately equally effective as catalysts for the isomerization of methylcyclopentane to cyclohexane at room temperature.

EXAMPLE III

This example illustrates the preparation of additional chlorided Pt/Al$_2$O$_3$ catalysts in accordance with the preparation method of this invention and their evaluation in alkane isomerization autoclave tests.

Catalyst F (Invention) was prepared substantially in accordance with the procedure for Catalyst C (described in Example I), except that the heating step using the H$_2$/CCl$_4$ gas mixture was carried out for 1 hour at 150° C. (in lieu of 225° C.).

Catalyst G (Invention) was prepared substantially in accordance with the procedure for Catalyst C (described in Example I), except that the heating step using the H$_2$/CCl$_4$ gas mixture was carried out for 1 hour at 400° C. (in lieu of 225° C.).

Catalyst H (Invention) was prepared substantially in accordance with the procedure for Catalyst E (described in Example I) except that the heating step using the H$_2$/CCl$_4$ gas mixture was carried out for 1 hour at 400° C. (in lieu of 225° C.).

Preliminary evaluations of the above-described Inventions Catalysts F, G, and H and of Invention Catalysts A, C and G (described in Example I) in batch n-hexane isomerization tests (carried out in an autoclave for 16 hours at room temperature; not described in detail herein) indicated that the catalysts prepared by chloriding with $H_2/CCl_4$ at a temperature of 250° C. generally were more active than the corresponding catalysts prepared by chloriding with $H_2/CCl_4$ at a temperature of 400° C. and 150° C., respectively. Based on these autoclave test results, it is concluded that the preferred temperature range for the second chloriding step (employing $H_2/HCl$ and $H_2/chloroalkane$, respectively) is about 180°–280° C. and that a range of about 200°–250° C. is particularly preferred.

EXAMPLE IV

This example illustrates the preparation of chlorided Pd- and Ni-containing alumina materials in accordance with this invention and their evaluation as catalysts in n-butane isomerization tests.

Catalyst I (Invention) contained 0.51 weight-% Pd and was prepared as follows. 38.0 grams of alumina (provided by United Catalysts, Inc., Louisville, Ky., under the product designation "CS-331") was impregnated by incipient wetness in air at room temperature with a solution of 3.8 grams of $Pd(NH_3)_2(NO_3)_2$ in 21.0 grams of water, followed by air-drying the Pd-impregnated alumina, calcining it in air for 6 hours at 525° C., and reducing it for 2 hours in flowing hydrogen gas at 425° C. A sample of 12.0 of this reduced material was then mixed with 2.00 grams of dry $AlCl_3$, heated for 10 hours in a helium stream (flow rate: 40 cc/minute) at 225° C. and for 2 hours in this He stream at 650° C., heated for 2 hours in a hydrogen/$CCl_4$ gas mixture (flow rate of $H_2$: 3 liter/hour; flow rate of $CCl_4$: 16 microliter/hour) at 225° C.

Catalyst J (Invention) contained 1.03 weight-% Ni and was prepared substantially in accordance with the procedure for Catalyst I, except that 38.0 grams of "CS-331" alumina were impregnated with a solution of 1.88 grams of $Ni(NO_3)_2 \cdot 6H_2O$ in 24.0 grams of water.

Catalyst K (Invention) contained 0.31 weight-% Pt and was prepared substantially in accordance with the procedure for Catalyst J, except that 38.0 grams of "CS-331" alumina were impregnated with a solution of $H_2PtCl_6$, 0.30 gram of HCl and 25.2 grams of water.

The above-described catalysts were evaluated for their n-butane isomerization activity substantially in accordance with the procedure described in Example II. Pertinent test results are summarized in Table II.

method of this invention) in the above-described n-butane isomerization tests.

Reasonable variations, modifications and adaptations for various usages and conditions can be made within the scope of the disclosure and the appended claims, without departing from the scope of this invention.

That which is claimed:

1. A method of preparing a solid Group VIII metal-and chlorine-containing composition which comprises:
   (1) mixing at least one aluminum-and chlorine-containing compound selected from the group consisting of aluminum chloride and alkyl aluminum chlorides with a solid material which comprises (I) at least one Group VIII metal selected from the group consisting of platinum, palladium and nickel and (ii) alumina as the support, wherein said solid material has been prepared by a method comprising:
      (a) impregnating an alumina material with at least one compound of a Group VIII metal selected from the group consisting of platinum, palladium and nickel;
      (b) calcining the impregnated alumina obtained in step (a) at a temperature of about 300°–650° C. for a time period of at least about 10 minutes; and
      (c) treating the calcined material obtained in step (b) with a reducing gas comprising free hydrogen at a temperature of about 200°–550° C. for a time period of at least about 10 minutes, and wherein the weight ratio of said at least one aluminum- and chlorine-containing compound to said solid material used in step (1) is in the range of about 0.05:1 to about 1:1;
   (2) heating the mixture obtained in step (1) in a substantially inert gas atmosphere at a temperature of about 450°–700° C. for a time period of at least about 10 minutes; and
   (3) treating the material obtained in step (2) with a gas mixture comprising hydrogen gas and at least one chlorine-containing compound selected from the group consisting of hydrogen chloride and chloroalkanes, at a temperature of about 50°–700° C. for a time period of at least about 10 minutes.

2. A method in accordance with claim 1, wherein said aluminum- and chlorine-containing compound used in step (1) is selected from the group consisting of methylaluminum dichloride, methylaluminum sesquichloride, dimethylaluminum chloride, ethylaluminum dichloride, ethylaluminum sesquichloride, diethylaluminum chloride, propylaluminum dichloride, dipropylaluminum chloride, butylaluminum dichloride, dibutylaluminum chloride and mixtures thereof.

3. A method in accordance with claim 1, wherein said at least one aluminum- and chlorine-containing compound is aluminum chloride.

TABLE II

| | | First Chlorination | | Second Chlorination | | n-Butane Isomerization | |
|---|---|---|---|---|---|---|---|
| Catalyst | Wt % Promoter(s) in Catalyst | Agent | Temp. (°C.) | Agent | Temp. (°C.) | Reaction Time (hr.) | % of Isobutane in Product |
| I (Invention) | 0.51% Pd | $AlCl_3$ | 650 | $H_2/CCl_4$ | 225 | 14 | 11.4 |
| J (Invention) | 1.03% Ni | $AlCl_3$ | 650 | $H_2/CCl_4$ | 225 | 14 | 12.6 |
| K (Invention) | 0.31% Pt | $AlCl_3$ | 650 | $H_2/CCl_4$ | 225 | 14 | 11.8 |

Test data in Table II show that the Pd- and Ni-containing catalysts (Catalysts I and J) were approximately as active as the Pt-containing Catalyst K (all obtained by the preparation 4. A method in accordance with claim 3, wherein the time period of step (2) is about 0.5–20 hours, the molar ratio of hydrogen to said at least one chlorine-containing compound in said gas mixture used in step (3) is about 0.01:1 to about 100:1, and the time period of step (3) is about 0.2–20 hours.

5. A method in accordance with claim 4, wherein said at least one chlorine-containing compound used in step (3) is selected from the group consisting of hydrogen chloride and chloroalkanes containing 1–4 carbon atoms per molecule and 1–6 chlorine atoms per molecule.

6. A method in accordance with claim 5, wherein the temperature in step (2) is about 625°–675° C., the time period of step (2) is about 0.5–2 hours, the molar ratio of hydrogen to said at least one chlorine-containing compound used in step (3) is about 0.05:1 to about 50:1, the temperature in step (3) is about 150°–400° C., and the time period of step (3) is about 0.5–2 hours.

7. A method in accordance with claim 6, where said at least one chlorine-containing compound used in step (3) is selected from the group, consisting of hydrogen chloride and carbon tetrachloride.

8. A method in accordance with claim 7, wherein the molar ratio of hydrogen to said at least one chlorine-containing compound used in step (3) is about 0.2:1 to about 20:1 and the temperature in step (3) is about 180°–280° C.

9. A method in accordance with claim 1, wherein at least one titanium compound is also present in step (1).

10. A method in accordance with claim 1, wherein step (b) is carried out for a time period of about 0.5–20 hours, and step (c) is carried out for a time period of about 0.5–20 hours.

11. A method in accordance with claim 1, wherein step (a) is carried out with at least one dissolved platinum compound.

12. A method in accordance with claim 11, wherein said alumina material is also impregnated with at least one dissolved titanium compound.

13. A method in accordance with claim 1, wherein step (a) is carried out with at least one dissolved palladium compound.

14. A method in accordance with claim 1, wherein step (a) is carried out with at least one dissolved nickel compound.

15. A method in accordance with claim 1, wherein the material obtained in step (3) comprises about 0.1–8 weight-% of said at least one Group VIII metal and about 2–7 weight-% chlorine.

16. A method in accordance with claim 15, wherein said at least one Group VIII metal is platinum.

17. A method in accordance with claim 15, wherein said at least one Group VIII metal is palladium.

18. A method in accordance with claim 15, wherein said at least one Group VIII metal is nickel.

19. A method in accordance with claim 15, wherein said material obtained in step (3) additionally comprises about 0.05–1 weight-% titanium.

* * * * *